(12) United States Patent
Music et al.

(10) Patent No.: US 8,160,726 B2
(45) Date of Patent: Apr. 17, 2012

(54) USER INTERFACE AND IDENTIFICATION IN A MEDICAL DEVICE SYSTEM AND METHOD

(75) Inventors: Doug Music, Livermore, CA (US); Darius D. Eghbal, Oakland, CA (US); Steve Vargas, Pleasanton, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 0 days.

(21) Appl. No.: 12/706,060

(22) Filed: Feb. 16, 2010

(65) Prior Publication Data

US 2010/0141391 A1 Jun. 10, 2010

Related U.S. Application Data

(62) Division of application No. 11/540,385, filed on Sep. 29, 2006, now Pat. No. 7,706,896.

(51) Int. Cl.
*G05B 11/01* (2006.01)
*G05B 15/00* (2006.01)

(52) U.S. Cl. .......................................... 700/17; 700/83

(58) Field of Classification Search .................. 700/17, 700/83
See application file for complete search history.

(56) References Cited

U.S. PATENT DOCUMENTS

| | | |
|---|---|---|
| 3,638,640 A | 2/1972 | Shaw |
| 4,475,901 A * | 10/1984 | Kraegen et al. ............ 604/67 |
| 4,621,643 A | 11/1986 | New, Jr. et al. |
| 4,653,498 A | 3/1987 | New, Jr. et al. |
| 4,700,708 A | 10/1987 | New, Jr. et al. |
| 4,714,341 A | 12/1987 | Hamaguri et al. |
| 4,770,179 A | 9/1988 | New, Jr. et al. |
| 4,805,623 A | 2/1989 | Jöbsis |
| 4,869,254 A | 9/1989 | Stone et al. |
| 4,911,167 A | 3/1990 | Corenman et al. |
| 4,936,679 A | 6/1990 | Mersch |
| 4,972,331 A | 11/1990 | Chance |
| 5,078,136 A | 1/1992 | Stone et al. |
| 5,119,815 A | 6/1992 | Chance |
| 5,122,974 A | 6/1992 | Chance |
| 5,167,230 A | 12/1992 | Chance |
| 5,297,548 A | 3/1994 | Pologe |
| 5,351,685 A | 10/1994 | Potratz |
| 5,355,880 A | 10/1994 | Thomas et al. |

(Continued)

FOREIGN PATENT DOCUMENTS

DE 19932147 1/2001

(Continued)

OTHER PUBLICATIONS

Lee, Jason C.S., et al., "Measurement of Percent Carboxyhemoglobin with Pulse-Oximetry Technique," *IEEE Engineering in Medicine & Biology Society 10th Annual International Conference*, CH2566-88, vol. 88, pp. 1781-1782 (1988).

(Continued)

*Primary Examiner* — Ronald Hartman, Jr.

(57) ABSTRACT

There are provided systems and methods for reading identification information and storing identification information in a medical device. More specifically, in one embodiment, there is provided a method for accessing a medical device, the method including reading identification information from an identification tag and storing identification information in the medical device as patient information of a patient identification system. Medical devices having a reader and patient identification system are also disclosed.

18 Claims, 10 Drawing Sheets

U.S. PATENT DOCUMENTS

| | | |
|---|---|---|
| 5,368,026 A | 11/1994 | Swedlow et al. |
| 5,372,136 A | 12/1994 | Steuer et al. |
| 5,385,143 A | 1/1995 | Aoyagi |
| 5,482,036 A | 1/1996 | Diab et al. |
| 5,533,507 A | 7/1996 | Potratz |
| 5,553,614 A | 9/1996 | Chance |
| 5,564,417 A | 10/1996 | Chance |
| 5,575,285 A | 11/1996 | Takanashi et al. |
| 5,630,413 A | 5/1997 | Thomas et al. |
| 5,645,059 A | 7/1997 | Fein et al. |
| 5,645,060 A | 7/1997 | Yorkey |
| 5,662,106 A | 9/1997 | Swedlow et al. |
| 5,692,503 A | 12/1997 | Kuenstner |
| 5,758,644 A | 6/1998 | Diab et al. |
| 5,779,631 A | 7/1998 | Chance |
| 5,830,139 A | 11/1998 | Abreu |
| 5,842,981 A | 12/1998 | Larsen et al. |
| 5,873,821 A | 2/1999 | Chance et al. |
| 5,935,099 A * | 8/1999 | Peterson et al. ............. 604/65 |
| 5,995,856 A | 11/1999 | Mannheimer et al. |
| 6,011,986 A | 1/2000 | Diab et al. |
| 6,035,223 A | 3/2000 | Baker |
| 6,064,898 A | 5/2000 | Aldrich |
| 6,120,460 A | 9/2000 | Abreu |
| 6,134,460 A | 10/2000 | Chance |
| 6,163,715 A | 12/2000 | Larsen et al. |
| 6,181,958 B1 | 1/2001 | Steuer et al. |
| 6,230,035 B1 | 5/2001 | Aoyagi et al. |
| 6,266,546 B1 | 7/2001 | Steuer et al. |
| 6,312,393 B1 | 11/2001 | Abreu |
| 6,359,612 B1 | 3/2002 | Peter et al. |
| 6,397,091 B2 | 5/2002 | Diab et al. |
| 6,398,744 B2 | 6/2002 | Bystrom et al. |
| 6,415,236 B2 | 7/2002 | Kobayashi et al. |
| 6,438,399 B1 | 8/2002 | Kurth |
| 6,445,597 B1 | 9/2002 | Boylan et al. |
| 6,478,800 B1 | 11/2002 | Fraser et al. |
| 6,487,439 B1 | 11/2002 | Skladnev et al. |
| 6,501,974 B2 | 12/2002 | Huiku |
| 6,501,975 B2 | 12/2002 | Diab et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,591,122 B2 | 7/2003 | Schmitt |
| 6,594,513 B1 | 7/2003 | Jobsis et al. |
| 6,606,509 B2 | 8/2003 | Schmitt |
| 6,615,064 B1 | 9/2003 | Aldrich |
| 6,618,602 B2 * | 9/2003 | Levin ............. 600/323 |
| 6,622,095 B2 | 9/2003 | Kobayashi et al. |
| 6,658,277 B2 | 12/2003 | Wasserman |
| 6,662,030 B2 | 12/2003 | Khalil et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,690,958 B1 | 2/2004 | Walker et al. |
| 6,693,812 B1 | 2/2004 | Li et al. |
| 6,708,048 B1 | 3/2004 | Chance |
| 6,711,424 B1 | 3/2004 | Fine et al. |
| 6,711,425 B1 | 3/2004 | Reuss |
| 6,748,254 B2 | 6/2004 | Chin et al. |
| 6,785,568 B2 | 8/2004 | Chance |
| 6,801,797 B2 | 10/2004 | Mannheimer et al. |
| 6,801,799 B2 | 10/2004 | Mendelson |
| 6,827,702 B2 * | 12/2004 | Lebel et al. ............. 604/67 |
| 6,873,865 B2 | 3/2005 | Steuer et al. |
| 6,934,571 B2 | 8/2005 | Wiesmann et al. |
| 6,949,081 B1 | 9/2005 | Chance |
| 6,954,148 B2 | 10/2005 | Pulkkinen et al. |
| 6,961,598 B2 | 11/2005 | Diab |
| 7,001,334 B2 | 2/2006 | Reed et al. |
| 7,027,849 B2 | 4/2006 | Al-Ali |
| 7,152,785 B2 * | 12/2006 | Metz et al. ............. 235/380 |
| 7,171,277 B2 | 1/2007 | Engleson et al. |
| 7,215,991 B2 | 5/2007 | Besson et al. |
| 7,231,263 B2 | 6/2007 | Choi |
| 7,248,933 B2 * | 7/2007 | Wildman ............. 700/90 |
| 7,323,991 B1 * | 1/2008 | Eckert et al. ............. 340/572.1 |
| 7,395,214 B2 | 7/2008 | Shillingburg |
| 7,404,796 B2 * | 7/2008 | Ginsberg ............. 600/365 |
| 7,423,526 B2 | 9/2008 | Despotis |
| 7,438,216 B2 * | 10/2008 | Ambekar et al. ............. 235/375 |
| 7,518,500 B2 * | 4/2009 | Aninye et al. ............. 340/506 |
| 7,643,965 B2 * | 1/2010 | Zhang ............. 702/191 |
| 7,698,002 B2 | 4/2010 | Music |
| 7,839,266 B2 * | 11/2010 | Hoglund et al. ............. 340/286.07 |
| 2001/0005773 A1 | 6/2001 | Larsen et al. |
| 2001/0016696 A1 | 8/2001 | Bystrom et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0038081 A1 | 3/2002 | Fein et al. |
| 2002/0038392 A1 * | 3/2002 | De La Huerga ............. 710/8 |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0125991 A1 * | 9/2002 | Levin ............. 340/5.8 |
| 2002/0133068 A1 | 9/2002 | Huiku |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0032867 A1 * | 2/2003 | Crothall et al. ............. 600/300 |
| 2003/0048312 A1 | 3/2003 | Zimmerman et al. |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0144878 A1 | 7/2003 | Wilkes et al. |
| 2003/0195402 A1 | 10/2003 | Fein et al. |
| 2003/0212379 A1 * | 11/2003 | Bylund et al. ............. 604/504 |
| 2003/0216974 A1 | 11/2003 | Browne |
| 2003/0220548 A1 | 11/2003 | Schmitt |
| 2003/0220576 A1 | 11/2003 | Diab |
| 2004/0006261 A1 | 1/2004 | Swedlow et al. |
| 2004/0010188 A1 | 1/2004 | Wasserman |
| 2004/0054270 A1 | 3/2004 | Pewzner et al. |
| 2004/0078231 A1 | 4/2004 | Wilkes et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0162472 A1 | 8/2004 | Berson et al. |
| 2004/0167465 A1 | 8/2004 | Mihai et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0183683 A1 * | 9/2004 | Funahashi ............. 340/573.1 |
| 2004/0186357 A1 | 9/2004 | Soderberg et al. |
| 2004/0230106 A1 | 11/2004 | Schmitt et al. |
| 2005/0022274 A1 * | 1/2005 | Campbell et al. ............. D24/100 |
| 2005/0052275 A1 | 3/2005 | Houle |
| 2005/0062603 A1 | 3/2005 | Fuerst et al. |
| 2005/0065465 A1 * | 3/2005 | Lebel et al. ............. 604/66 |
| 2005/0080323 A1 | 4/2005 | Kato |
| 2005/0101850 A1 | 5/2005 | Parker |
| 2005/0107676 A1 | 5/2005 | Acosta et al. |
| 2005/0108057 A1 | 5/2005 | Cohen et al. |
| 2005/0113656 A1 | 5/2005 | Chance |
| 2005/0168722 A1 | 8/2005 | Forstner et al. |
| 2005/0192488 A1 | 9/2005 | Bryenton et al. |
| 2005/0203357 A1 | 9/2005 | Debreczeny et al. |
| 2005/0234317 A1 | 10/2005 | Kiani et al. |
| 2005/0234381 A1 | 10/2005 | Niemetz et al. |
| 2005/0247319 A1 | 11/2005 | Berger |
| 2005/0267346 A1 | 12/2005 | Faber et al. |
| 2005/0280531 A1 | 12/2005 | Fadem et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0025660 A1 | 2/2006 | Swedlow et al. |
| 2006/0030762 A1 | 2/2006 | David et al. |
| 2006/0030763 A1 | 2/2006 | Mannheimer et al. |

| | | | |
|---|---|---|---|
| 2006/0030765 A1 | 2/2006 | Swedlow et al. | |
| 2006/0032918 A1 | 2/2006 | Andreasson et al. | |
| 2006/0047538 A1* | 3/2006 | Condurso et al. | 705/3 |
| 2006/0052680 A1 | 3/2006 | Diab | |
| 2006/0058683 A1 | 3/2006 | Chance | |
| 2006/0069319 A1 | 3/2006 | Elhag et al. | |
| 2006/0079794 A1 | 4/2006 | Liu et al. | |
| 2006/0132283 A1 | 6/2006 | Eberhart et al. | |
| 2006/0155589 A1 | 7/2006 | Lane et al. | |
| 2006/0185005 A1 | 8/2006 | Graves et al. | |
| 2006/0211932 A1 | 9/2006 | Al-Ali et al. | |
| 2006/0276714 A1 | 12/2006 | Holt et al. | |
| 2007/0033068 A1 | 2/2007 | Rao et al. | |
| 2007/0124002 A1* | 5/2007 | Estes et al. | 700/20 |
| 2007/0180047 A1 | 8/2007 | Dong et al. | |
| 2007/0258626 A1 | 11/2007 | Reiner | |
| 2007/0267475 A1* | 11/2007 | Hoglund et al. | 235/375 |
| 2008/0004513 A1 | 1/2008 | Walker et al. | |
| 2008/0081956 A1 | 4/2008 | Shah | |
| 2008/0082338 A1 | 4/2008 | O'Neil | |
| 2008/0082339 A1 | 4/2008 | Li | |
| 2008/0097175 A1 | 4/2008 | Boyce | |
| 2008/0097176 A1 | 4/2008 | Music | |
| 2008/0097177 A1 | 4/2008 | Music | |
| 2008/0194925 A1 | 8/2008 | Alsafadi et al. | |
| 2008/0208009 A1 | 8/2008 | Shikarski | |

FOREIGN PATENT DOCUMENTS

| | | |
|---|---|---|
| DE | 102 13 692 A1 | 10/2003 |
| EP | 1643401 | 4/2006 |
| JP | 5-212016 | 8/1993 |
| WO | WO 92/20273 | 11/1992 |
| WO | WO 94/03102 | 2/1994 |
| WO | WO 97/49330 | 12/1997 |
| WO | WO 01/45553 A1 | 6/2001 |
| WO | WO0237466 | 5/2002 |
| WO | WO2005114524 | 12/2005 |
| WO | WO2006006107 | 1/2006 |
| WO | WO2006006158 | 1/2006 |
| WO | WO2006009830 | 1/2006 |
| WO | WO2006048840 | 5/2006 |
| WO | WO2006051464 | 5/2006 |
| WO | WO2006064397 | 6/2006 |
| WO | WO2006109072 | 10/2006 |
| WO | WO2007071180 | 6/2007 |
| WO | WO2007131064 | 11/2007 |
| WO | WO2008004205 | 1/2008 |
| WO | WO2006087689 | 8/2008 |

OTHER PUBLICATIONS

Lee, Jason C.S., et al., "Simultaneous Measurement of Percent Carboxyhemoglobin and Functional Oxygen Saturation," *IEEE Engineering in Medicine and Biology Society*, CH2770-6, vol. 89, pp. 1092-1093 (1989).

Bongard, Frederic S., "Continuous Dual Oximetry in Surgical critical care—Indications and Limitations." *Annals of Surgery*, vol. 216. No. 1, pp. 60-68 (1992).

Herman, Bruce, MD. et al., "Assessment of Dysphagia with the Use of Pulse Oximetry", Dysphagia 14:152-156; Copyright Springer-Verlag New York Inc. (1999).

Tsien, Christine L., "TrendFinder: Automated Detection of Alarmable Trends", Massachusetts Institute of Technology, 241 pages (Jun. 2000).

ISR, PCT/US2007/020847, 6 pages, mailed Jun. 6, 2008.

Definition of "physiological", 1 page.

Wikipedia—Definition of "Pulse Oximeter"; 3 pages.

eNewsletter—Access Control Newsletter; 3 pages.

Internet Archive Wayback Machine; 1 page.

Cardax Command Centre; "New Product Profile"; 2 pages.

Cardax Command Centre; "Technical Spec"; 2 pages.

News; Cardax FT version 4.2 released; 2 pages.

\* cited by examiner

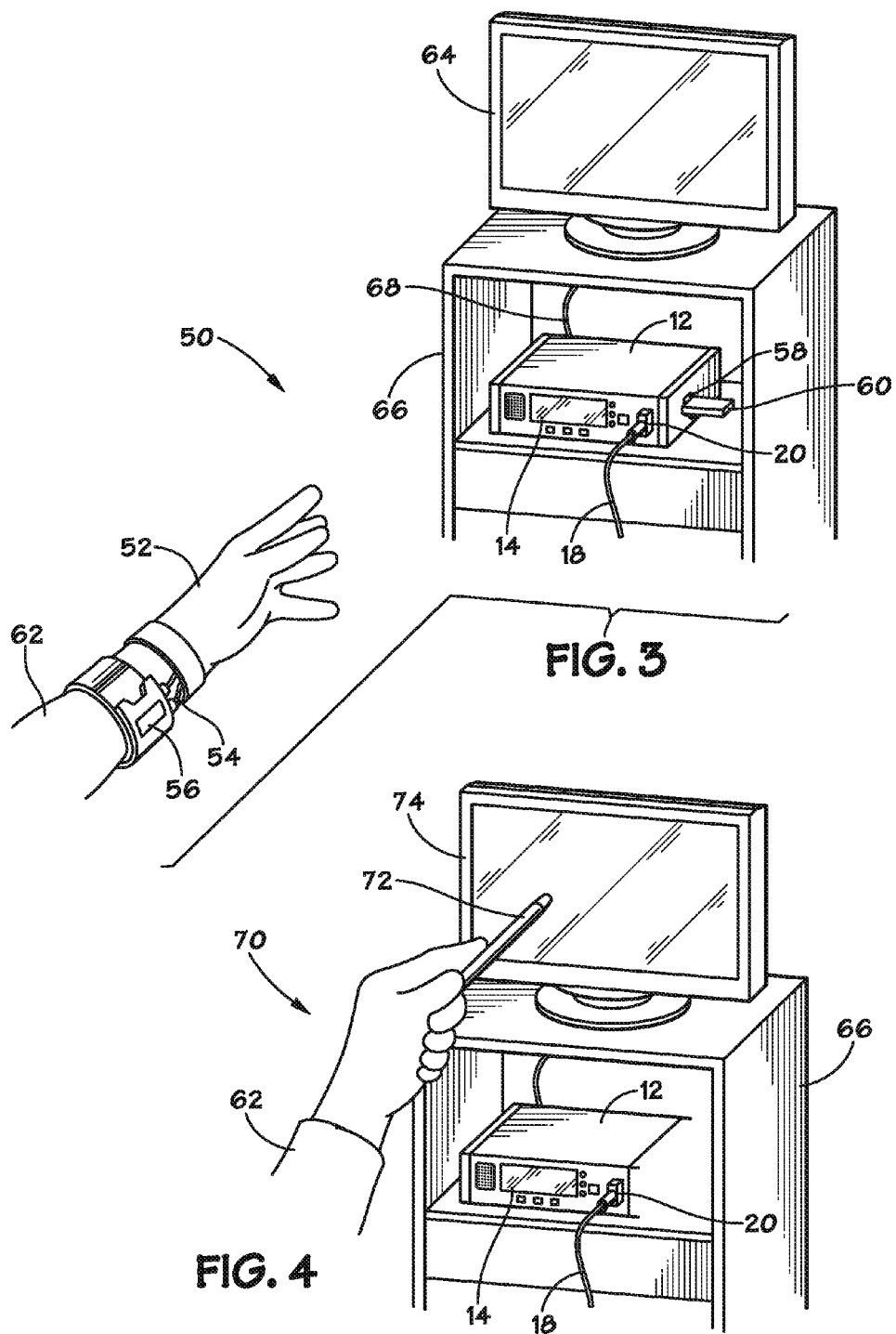

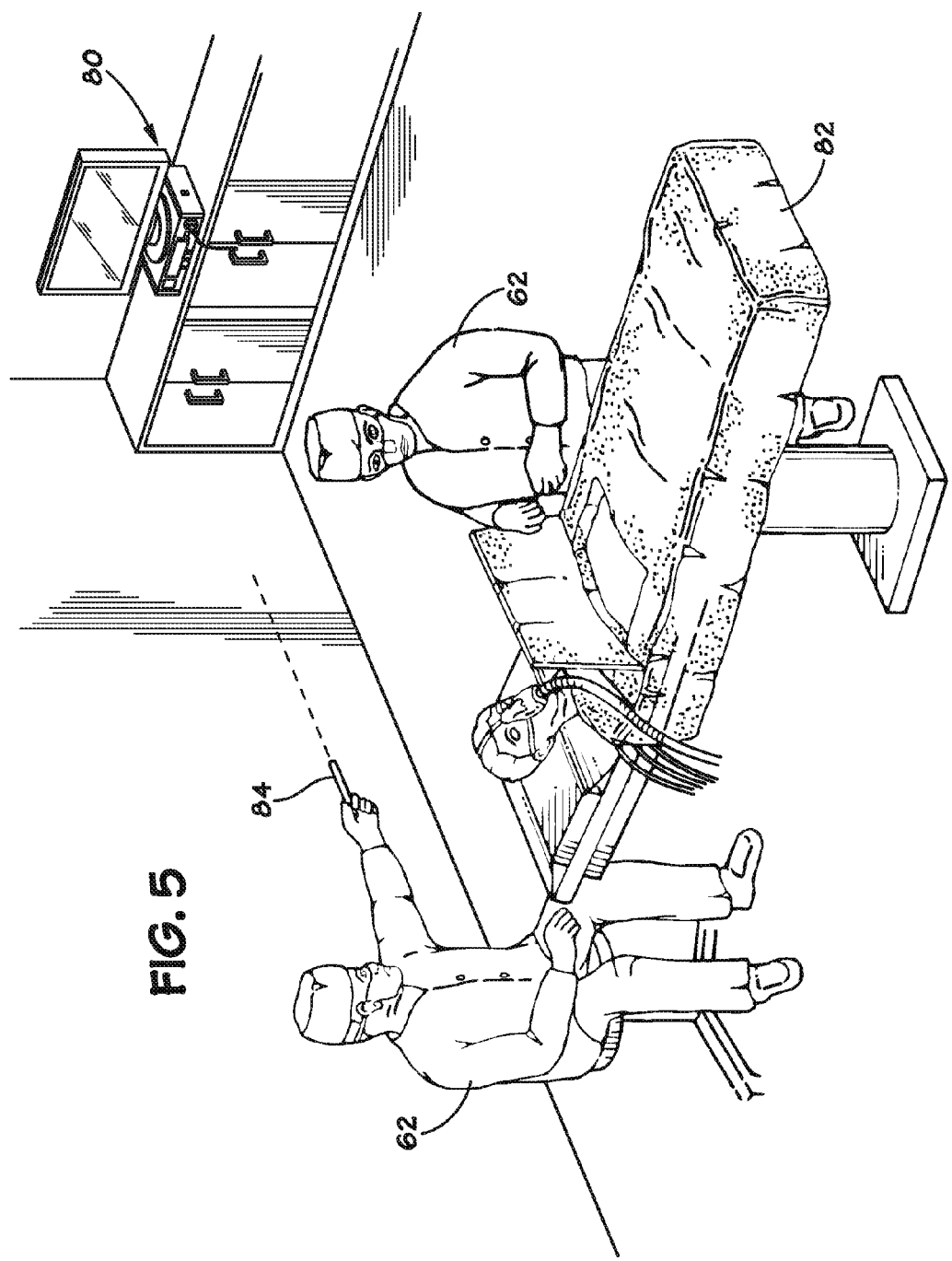

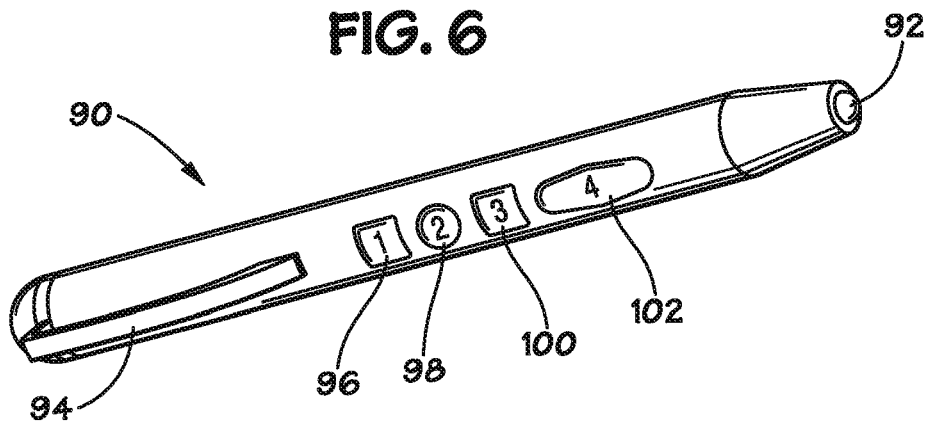
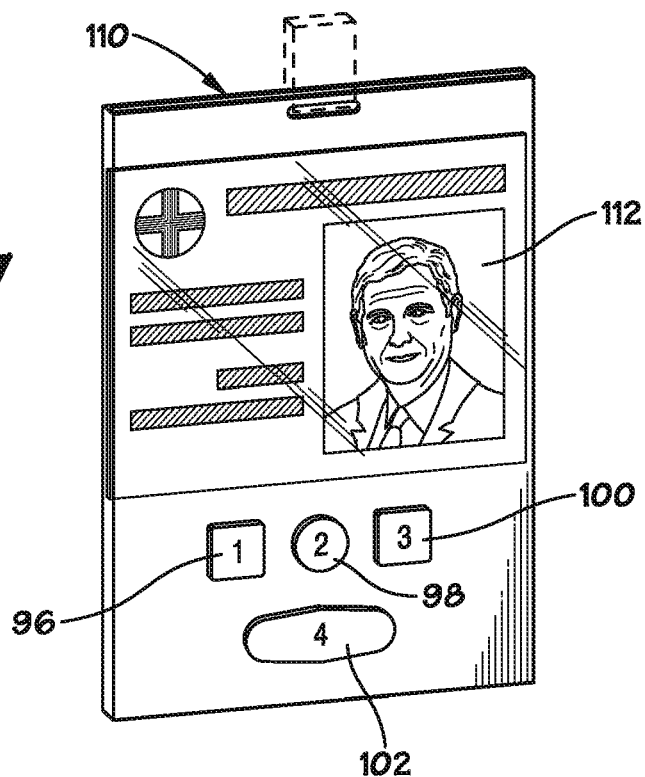
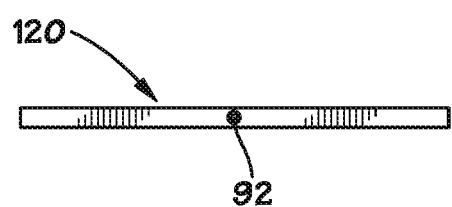

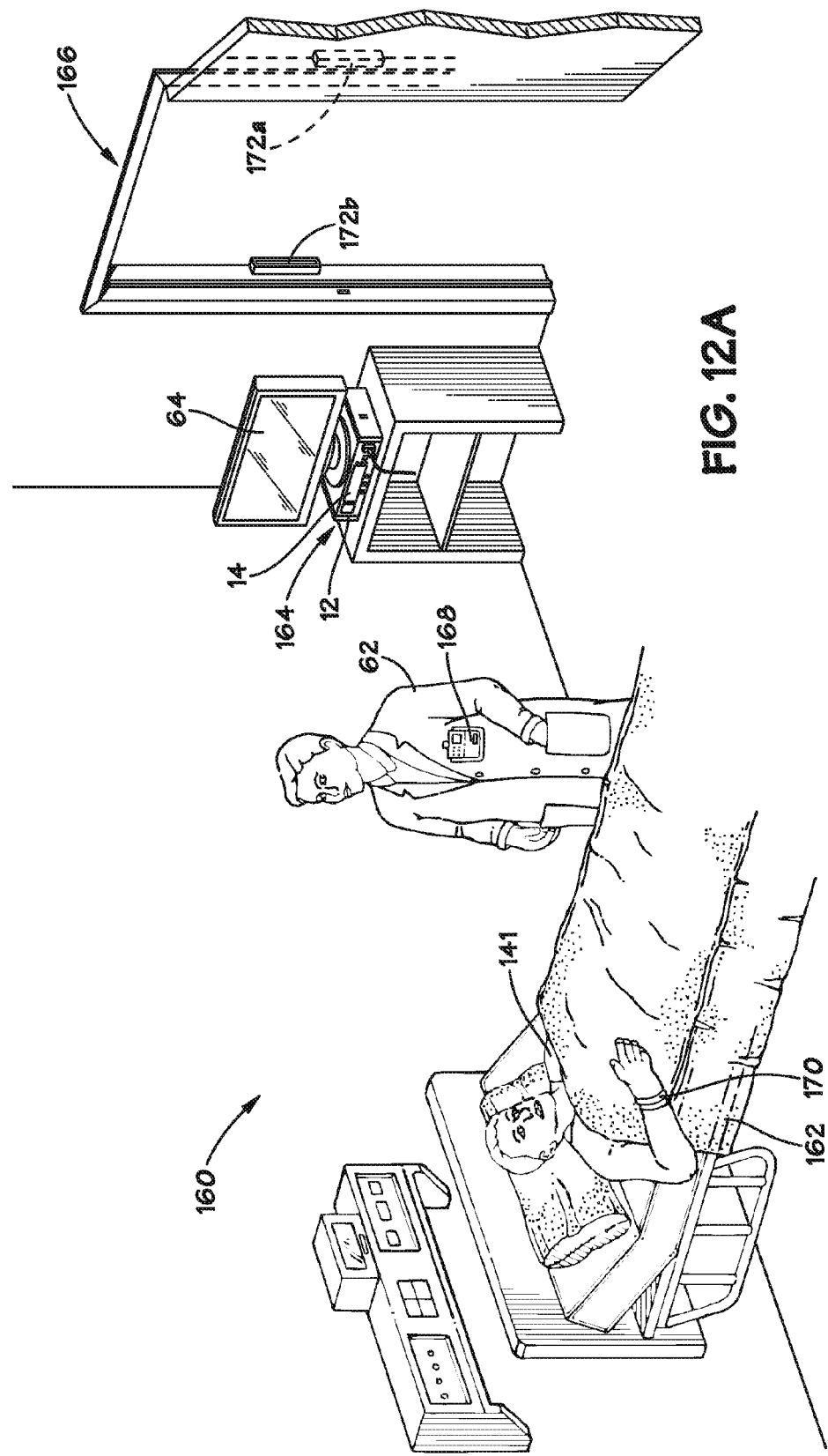

USER INTERFACE AND IDENTIFICATION IN A MEDICAL DEVICE SYSTEM AND METHOD

CROSS-REFERENCE TO RELATED APPLICATION

This application is a divisional of U.S. application Ser. No. 11/540,385, filed on Sep. 29, 2006, the disclosure of which are hereby incorporated by reference in their entirety for all purposes.

BACKGROUND OF THE INVENTION

1. Field Of The Invention

The present invention relates generally to medical devices and, more particularly, to user interfaces and identification systems integrated with medical devices.

2. Description Of The Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide caregivers, such as doctors, nurses, and/or other healthcare personnel, with the information they need to provide the best possible healthcare for their patients. As a result, such monitoring devices have become an indispensable part of modern medicine.

For example, one technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters and other medical devices are typically mounted on stands that are positioned around a patient's bed or around an operating room table. When a caregiver desires to command the medical device (e.g., program, configure, and so-forth) they manipulate controls or push buttons on the monitoring device itself. The monitoring device typically provides results or responses to commands on a Liquid Crystal Diode ("LCD") screen mounted in an externally visible position within the medical device.

This conventional configuration, however, has several disadvantages. First, as described above, this conventional configuration relies upon physical contact with the monitoring device to input commands (e.g., pushing a button, turning a knob, and the like). Such physical contact, however, raises several concerns. Among these concerns are that in making contact with the medical device, the caregiver may spread illness or disease from room to room. More specifically, a caregiver may accidentally deposit germs (e.g., bacteria, viruses, and so forth) on the medical device while manipulating the device's controls. These germs may then be spread to the patient when a subsequent caregiver touches the medical device and then touches the patient. Moreover, if medical devices are moved from one patient room to another, germs transferred to the medical device via touch may be carried from one patient room to another. Even in operating rooms where medical devices are typically static, germs may be transferred onto a monitoring device during one surgery and subsequently transferred off the medical device during a later performed surgery.

Second, beyond contamination, medical devices that rely on physical contact for command input may create clutter the caregiver's workspace. For example, because the medical device must be within an arm's length of the caregiver, the medical device may crowd the caregiver—potentially even restricting free movement of the caregiver. In addition, caregivers may have difficulty manipulating controls with gloved hands. For example, it may be difficult to grasp a knob or press a small button due to the added encumbrance of a latex glove.

Third, current trends in general medical device design focus on miniaturizing overall medical device size. However, as controls which rely on physical contact must be large enough for most, if not all, caregivers to manipulate with their hands, monitoring devices that employ these types of controls are limited in their possible miniaturization. For example, even if it were possible to produce a conventional oximeter that was the size of a postage stamp, it would be difficult to control this theoretical postage stamp-sized pulse oximeter with currently available techniques.

Additionally, even as medical devices become smaller, the need for secured access remains prevalent. First, medical device alerts and alarms often require the attention of a caregiver to ensure patient health. Access to medical devices by non-caregivers could result in ineffective patient care. Second, the recently passed Health Insurance Portability and Accountability Act ("HIPPA") regulates patient privacy and security. HIPPA privacy standards require the protection of patient data from inappropriate and unauthorized disclosure or use, and HIPPA security standards require physical safeguards to protect access to equipment containing patient data. As user interfaces evolve, new methods of providing secured access will be desirable. For example, traditional entry screens can be secured using passwords. However, as device interfaces evolve to eliminate entry screens, the traditional password protection process may no longer by feasible.

In addition, conventional techniques for outputting medical data also have several potential drawbacks. For example, as described above, conventional techniques for displaying outputs rely on LCD screens mounted on the medical device itself. Besides constantly consuming power, these LCD screens must be large enough to be visually accessed by a caregiver. As such, the conventional LCD screens employed in typical medical devices also may be a barrier towards miniaturization of the medical device. Further, conventional screen-based output techniques may be impersonal to the patient and may lack configurability by the caregiver.

For at least the reasons set forth above, improved systems and methods for interfacing with and being identified by a medical device would be desirable.

BRIEF DESCRIPTION OF THE DRAWINGS

Advantages of the invention may become apparent upon reading the following detailed description and upon reference to the drawings in which:

FIG. 3 is a diagrammatical representation of a medical device including another gesture interface in accordance with one embodiment of the present invention;

FIG. 4 is a diagrammatical representation of a pulse oximeter configured with a pen-based interface in accordance with one embodiment of the present invention;

FIG. 5 is a diagram of an operating room and a medical device including a laser-based interface in accordance with one embodiment of the present invention;

FIG. 6 is a diagrammatical representation of a remote control for interfacing with a medical device, in accordance with one embodiment of the present invention;

FIG. 7 is a diagrammatical representation of a remote control for interfacing with a medical device incorporated into a badge holder in accordance with one embodiment of the present invention;

FIG. 8 is a bottom view of the badge holder of FIG. 7 in accordance with one embodiment of the present invention;

FIG. 12A is a diagram of an exemplary hospital room configured to identify caregivers or patients in accordance with one embodiment of the present invention;

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
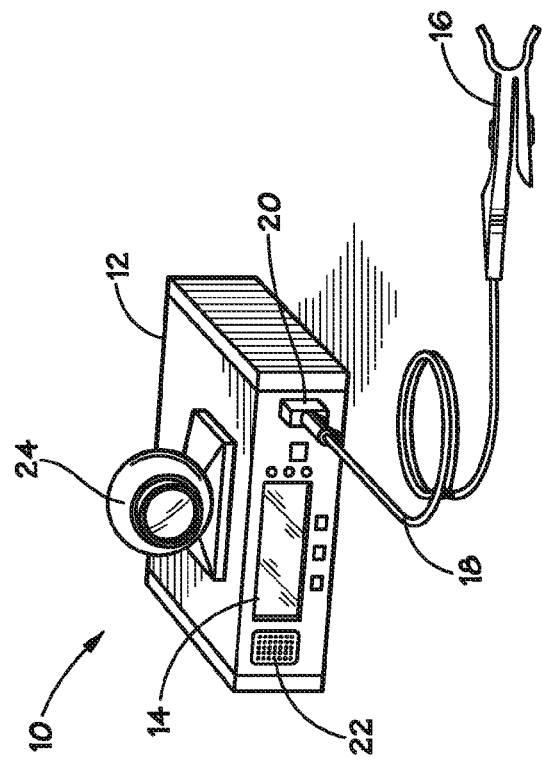
FIG. 1 is a diagrammatical representation of a medical device including a gesture interface in accordance with one embodiment of the present invention.

Turning initially to FIG. 1, an exemplary medical device including a gesture interface is illustrated and generally designated by a reference numeral 10. For example, in the illustrated embodiment, the medical device 10 comprises a pulse oximeter. The medial device 10 may include a main unit 12 that houses hardware and/or software configured to calculate various physiological parameters or produce various medical outputs. As illustrated, the main unit 12 may include a display 14 for displaying the calculated physiological parameters, such as oxygen saturation or pulse rate, to a caregiver or patient. In alternate embodiments, as described in further detail below, the display 14 may be omitted from the main unit 12.

The medical device 10 may also include a sensor 16 that may be connected to a body part (e.g., finger, forehead, toe, or earlobe) of a patient or a user. The sensor 16 may be configured to emit signals or waves into the patient's or user's tissue and detect these signals or waves after dispersion and/or reflection by the tissue. For example, the sensor 16 may be configured to emit light from two or more light emitting diodes ("LEDs") into pulsatile tissue (e.g., finger, forehead, toe, or earlobe) and then detect the transmitted light with a light detector (e.g., a photodiode or photo-detector) after the light has passed through the pulsatile tissue.

As those of ordinary skill in the art will appreciate, the amount of transmitted light that passes through the tissue generally varies in accordance with a changing amount of blood constituent in the tissue and the related light absorption. On a beat-by-beat basis, the heart pumps an incremental amount of arterial blood into the pulsatile tissue, which then drains back through the venous system. The amount of light that passes through the blood-perfused tissue varies with the cardiac-induced cycling arterial blood volume. For example, when the cardiac cycle causes more light-absorbing blood to be present in the tissue, less light travels through the tissue to strike the sensor's photo-detector. These pulsatile signals allow the medical device 10 to measure signal continuation caused by the tissue's arterial blood, because light absorption from other tissues remains generally unchanged in the relevant time span.

In alternate embodiments, the sensor 16 may take other suitable forms beside the form illustrated in FIG. 1. For example, the sensor 16 may be configured to be clipped onto a finger or earlobe or may be configured to be secured with tape or another static mounting technique. The sensor 16 may be connected to the main unit 12 via a cable 18 and a connector 20. Additionally, the medical device 10 may also include a speaker 22 to broadcast alarms or alerts.

The pulse oximeter main unit 12 may also include an integral camera 24. As will be described further below, the integral camera 24 may be configured to receive gesture commands from a caregiver or user that can be processed into commands for the medical device 10. Although FIG. 1 illustrates the integral camera 24 as being located on a top surface of the main unit 12, it will be appreciated that in alternate embodiments, the integral camera 24 may be located at another suitable location on or within the main unit 12, such as the front or side facades.

In alternate embodiments, instead of an integral camera, an external camera, such as a universal serial bus ("USB") web camera, may be connected to the main unit 12 via a cable and connector. The external camera may also be wirelessly connected to the main unit 12 via radio, infrared, or optical signals. For example, wireless local area networking ("WLAN") standards, such as Wi-Fi or Bluetooth may be used. Additionally, multiple cameras may be used to reduce the effects of parallax and occlusions. The cameras may be all external cameras, all integral cameras, or a combination of external and integral cameras.

Figure 2:
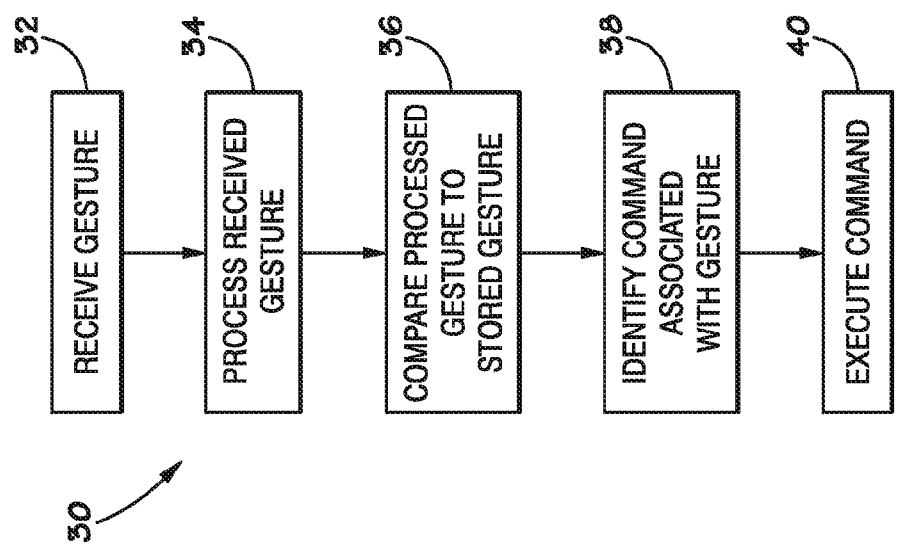
FIG. 2 is a flowchart illustrating an exemplary technique for processing a gesture command in accordance with one embodiment of the present invention.

FIG. 2 illustrates a flowchart of technique 30 for processing a gesture command in accordance with one embodiment. In one embodiment, the technique 30 may be executed by the medical device 10. In other embodiments, other medical devices, such as a respirator, cardiac monitor, or multi-parameter monitoring system, may execute the technique 30.

As indicated by block 32 of FIG. 2, the technique 30 may begin by receiving a gesture. For example, the camera 24 of medical device 10 may be configured to detect hand gestures. When a caregiver performs a hand gesture in front of the camera 24 the medical device 10 first receives one or more images of the gesture (block 32) via the camera 24 and then processes the gesture (block 34). As those of ordinary skill in the art will appreciate, the camera 24 may be an analog camera that converts the gesture into an analog signal and feeds it into a digitizer board, or the camera 24 may be a digital camera that records the gesture as a digital signal. In alternate embodiments, the camera 24 may be configured to detect other gestures originating from another bodily motion or state, such as arm gestures, finger pointing, hand poses, or facial expressions.

Returning to flowchart 30, the gesture processing, as indicated by block 34, may be performed by a gesture processing system integrated into the medical device 10. For example, during processing, images captured from the gesture may be normalized, enhanced, or transformed, and then features may be extracted from the images. Next, the processed gesture may be compared to a gesture database, as indicated by block 36. The gesture database may be pre-populated or programmed with a plurality of feature combinations that are associated with commands for the medical device 10. For example, feature combinations associated with the gesture command "turn alarm off" may be associated with a command for the medical device 10 to silence an alarm. However, in alternate embodiments the feature combinations may be programmed into the gesture database using a gesture training program. Additionally, in still other embodiments, the gesture processing may be located in an external central processing unit connected to the medical device 10 via a cable or by wireless technology such as radio, infrared, or optical signals.

After the gesture is compared to a gesture database, a command associated with the gesture may be identified, as indicated by block 38. For example, a hand gesture consisting of passing a hand over the camera from right to left with the palm facing the camera may be programmed into the gesture database to correspond with the command "turn alarm off." Once the gesture is identified in the gesture database, the command may be executed, as indicated by block 40. For example, the command to turn off the alarm may be transmitted to a medical device control system which would turn off the alarm.

Turning next to FIG. 3, an exemplary medical device including another gesture interface is illustrated and generally designated by a reference numeral 50. In addition to the main unit 12, the display 14, and the cable 18 for connection to the sensor 16 (not shown), the medical device 50, which may be a pulse oximeter, may include a tracking glove 52. As will be described further below, the tracking glove 52 may be configured to receive gesture commands from a caregiver 62 or user. As with the gesture command described in regard to FIG. 2, these gesture commands can be processed into commands for the medical device 50.

The tracking glove 52 may include a battery pack 56 connected to the tracking glove 52 via a cable. Although the battery pack is worn on the forearm in this embodiment, in alternative embodiments the battery pack may be located in other locations such as around the waist of the caregiver 62. Additionally, in other embodiments, the tracking glove 52 may be replaced by another tracking device such as a finger sensor. In yet another embodiment, the tracking glove 52 may have a light emitting diode ("LED") located on the glove and a software programmable switch to permit other functions to be directly programmed into the glove. For example, a button may be included on the glove that can be programmed so that when a caregiver presses the button an alarm on the medical device 50 is silenced.

In one embodiment, the caregiver 62 may make hand gestures while wearing the tracking glove 52. The tracking glove 52 may then record the movement (i.e., the gesture) and transmit the gesture to the medical device 50 via a wireless receiver 60 connected to the medical device 50. In alternate embodiments, the tracking glove 52 may communicate with a wireless receiver integrated into the main unit 12 or may be connected to the medical device 50 via a cable such as a fiber optic cable or a serial cable.

Similar to the medical device 10, the medical device 50 may be configured to interpret the tracking glove 52 movement and execute a command associated with the movement. For example, a hand movement, such as making a fist, may be associated with the command "turn alarm off." As such, when the caregiver 62 makes a fist while wearing the tracking glove 52, the medical device 50 may interpret the movement and sends a signal to the medical device 50 to silence an alarm.

In addition, in some embodiments, the medical device 50 may include calibration software which may allow a caregiver 62 to program movement combinations into the gesture database within the medical device. Additionally, in other embodiments, the gesture database may be located in an external central processing unit connected to the medical device 50 via a cable or by wireless technology such as radio, infrared, or optical signals.

Turning next to FIG. 4, an exemplary medical device configured with a pen-based interface is illustrated and generally designated by the reference numeral 70. In addition to the main unit 12, the display 14, and the cable 18 for connection to the sensor 16 (not shown), the medical device 70 may include a stylus 72. As will be described further below, the caregiver 62 may use the stylus 72 to control the medical device 70.

In one embodiment, the medical device 70 may have a separate display screen 74 connected to the main unit 12 via a cable or wireless means such as radio, infrared, or optic signals. The display screen 74 may be a touch screen with selection boxes corresponding to medical device commands. For example, when the caregiver 62 touches the stylus 72 to the selection box corresponding to "turn alarm off," the display screen 74 may transmit a signal to the main unit 12 which silences the alarm. In an alternate embodiment, the caregiver 62 may touch the screen directly without using the stylus. In still other embodiments, the stylus 72 may be used to touch selection boxes directly on the medical device 70, and the separate display 74 may be omitted.

In yet another embodiment, the stylus 72 may be used to draw symbols or characters representative of medical device commands on the display screen 74. In the embodiment illustrated in FIG. 4, the medical device 70 main unit 12 may include symbol recognition software which recognizes the symbols drawn on the display 74 and executes commands corresponding to the recognized symbols. For example, the letter "L" may be associated with the command "lower alarm limit." When a caregiver 62 draws an "L" on the display 74 the symbol recognition software may interpret the symbol, and the medical device 70 may lower the alarm limit by a predetermined amount. The symbol recognition software may be pre-populated or programmed with a plurality of symbols associated with medical device commands. In alternate embodiments, the symbol recognition software may include a calibration program to allow the caregiver 62 to associate symbols with medical device commands.

In still other embodiments, the stylus 72 may include an ultrasound transmitter. In this embodiment, the ultrasound transmitter may be configured to transmit movements of the stylus 72 back to the medical device 70 or another suitable receiver. For example, in one embodiment, the movements of the stylus 72 may be tracked by one or more sensors positioned around an operating room and coupled to the medical device 70.

Turning now to FIG. 5, an exemplary operating room and a medical device 80 including a laser-based interface in accordance with on embodiment is illustrated. In addition to the main unit 12, the display 14, and the cable 18 for connection to the sensor 16 (not shown), the medical device 80 may include a laser wand 84 and/or the display 64. As will be described further below, the caregiver 62 may use the laser wand 84 to control the medical device 80. It will be appreciated, however, that the operating room shown in FIG. 5 is merely one possible application of the medical device 80. Accordingly, the medical device 80 may be employed in patients' rooms, doctors' offices, or other suitable locations. Moreover, it will also be appreciated that the medical devices described in regard to FIGS. 1, 3, and 4, as well as those described below, may be employed in each of these locations as well.

In one embodiment, the caregiver 62 may be able to use the laser wand 84 to position a cursor on the display 64. For example, the caregiver 62 may focus a laser pointer dot on the display 64. As one skilled in the art will appreciate, a location of a laser pointer dot can be translated to the cursor position on a display 64. In alternate embodiments, the laser pointer dot may alternatively be focused on the display 14. In one embodiment, the display 64 (or the display 14) may employ a camera, such as the camera 24 discussed above, to detect the laser pointer dot. In various embodiments, the camera may be internal to the display 64 or may be externally connected to it via a cable or wirelessly. However, it will be appreciated that in still other embodiments, other suitable laser pointer detection techniques may be employed.

In one embodiment, the display 64 may contain a plurality of selection boxes or regions corresponding to commands for medical device 80. For example, the display 64 may contain a selection box for the command "turn alarm off." When the caregiver 62 focuses the laser pointer dot on one of the selection boxes for a minimum period of time, the software within the medical device 80 may first position the cursor at the selection box location. As the caregiver 62 continues to focus the laser pointer dot on the same selection box, the software within the medical device 80 may then select the box and execute the command associated with the selection box. In this example, the software may then silence the alarm.

In other embodiments, the laser wand 84 may have an integrated selection button. Once the caregiver 62 has positioned the cursor on the selection box, the caregiver 62 may then push the button to select the box and execute the pulse oximeter command associated with the box. The integrated selection button may employ standard remote control technology, such as transmitting an infrared signal to an infrared receiver integrated into the medical device 80. In alternate embodiments, an external receiver connected to the medical device 80 via a cable may be used.

As shown in FIG. 5, the laser wand 84 may allow the medical device 80 to be controlled from a distance by the caregiver 62. Consequently, the medical device 80 may be placed at a location away from the patient 82 allowing the caregivers 62 more room to maneuver. In some embodiments, each of the caregivers 62 may have their own laser wand 84 to further reduce the risks of cross-contamination.

In another embodiment, the medical device 80 may be controlled using a remote control style wand 90, as illustrated in FIG. 6. The wand 90 may contain a plurality of buttons each programmed to correspond to one or more medical device commands. For example, the buttons may be programmed as follows: the button labeled "1" 96 may be programmed to correspond to the command "Raise Alarm Limit;" the button "2" 98 may be programmed to correspond to the command "Lower Alarm Limit;" the button "3" 100 may be programmed to correspond to the command "Reset Alarm Limits;" and the button "4" 102 may be programmed to correspond to the command "Turn Alarm Off." It will be appreciated that these commands are exemplary. Although the buttons 96-102 are shown in FIG. 6 as being labeled with numbers and of certain shapes and sizes, in other embodiments, the buttons may be customized with different shapes, sizes, and labels. Additionally, the number of buttons present on the wand 90 may vary. The wand 90 also may contain a pen-style clip for attaching the wand 90 to the caregiver 62.

In the above-described embodiment, the wand 90 may contain a light emitting diode ("LED") 92 that transmits light pulses or infrared signals corresponding to a medical device command. For example, when a caregiver 62 presses button "1" 96, an integrated circuit within the wand 90 may send a command to the LED 92. The LED 92 may then send out a signal corresponding to this command. A receiver integrated into the medical device may receive the signal and respond by raising the alarm limit by a predetermined unit.

In other embodiments, the LED transmitter 92 may alternatively be replaced by a radio frequency ("rf") transmitter. In such an embodiment, the medical device 80 may include an integrated rf receiver. Additionally, in alternate embodiments, the rf transmitter may employ the Bluetooth radio frequency standard or other suitable standard.

The technology of the wand 90 may also be incorporated in other packages. For example, in one alternate embodiment, it may be incorporated into a badge holder, as illustrated in FIG. 7. The badge holder 110, in addition to holding a caregiver's badge 112, may also contain the several command buttons 96-102. As shown in the bottom view of FIG. 8, the badge holder 110 may also contain the transmitter 92 on the bottom of the badge holder 110. In alternate embodiments the transmitter 92 may be located on another facade such as the top, front, or sides of the badge holder 110. Additionally, in still other alternate embodiments, the control buttons 96-102 may be of various shapes and sizes and be located on other facades of the badge holder 110.

Figure 9:
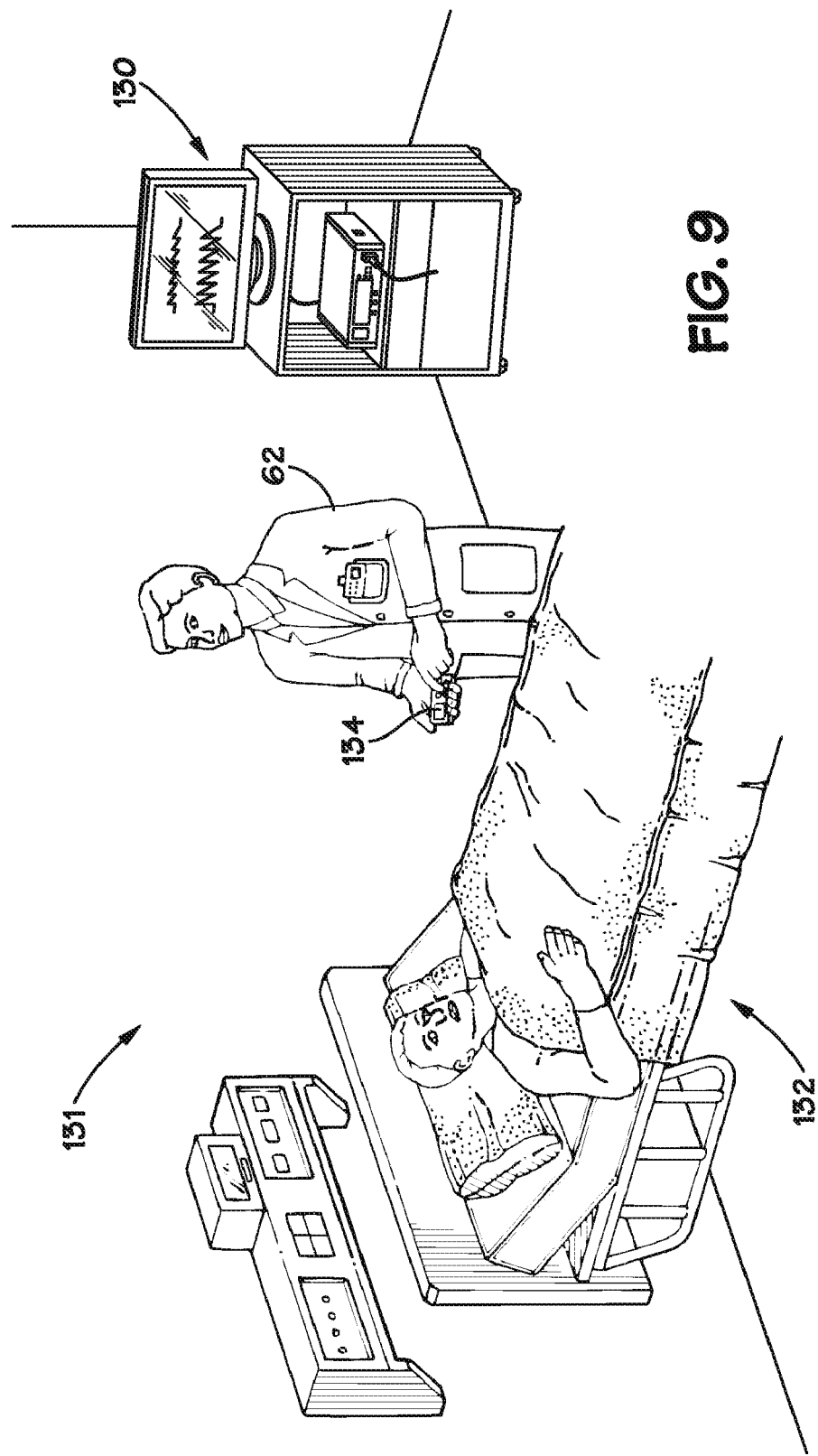
FIG. 9 illustrates a patient room and a medical device configured to interface with a personal digital assistant in accordance with one embodiment of the present invention.

Turning now to FIG. 9, an exemplary patient's room 131 and medical device 130 configured to interface with a personal data assistant ("PDA") 134 is illustrated. In addition to the main unit 12, the display 14, and the cable 18 for connection to the sensor 16 (not shown), the medical device 130 may include a PDA 134. As will be described further below, the caregiver 62 may use the PDA 134 to control the medical device 130. For example, the PDA 134 may be configured to present the caregiver 62 with one or more buttons or selectable locations on its screen that correspond to medical device controls or commands. Accordingly, when the caregiver 62 selects one of these controls or commands, the PDA 134 may be configured to transmit this control or command back to the medical device 130, which may subsequent execute the control or command. For example, the PDA 134 may be configured to generate a volume control display for the medical device 130. Upon accessing this volume display on the PDA 134, the caregiver may adjust the volume of the medical device 130 up or down.

Advantageously, the PDA 134 enables the caregiver 62 to control medical device 130 without physically touching or manipulating it. In addition, the PDA 134 may also supplement a display on the medical device 130. In particular, the PDA 134 may be configured to mirror or reproduce some or all of the contents displayed on the medical device's 130 internal display. In this way, the medical device 130 could advantageously be located away from the patient bed 132 or the caregiver 62, possibly even out of sight, as the inputs and outputs to the medical device 130 can be supported by the PDA 134.

Furthermore, the PDA 134 may be configured to interface with a plurality of medical devices 130 in a plurality of patient rooms 131. For example, a hospital may issue each of each caregivers 62 their own PDA 134, which they may use to access and/or control medical devices within a plurality of patient rooms. More specifically, the caregiver 62 may use their PDA 134 to access one or more medical devices within a first patient's room and then use the same PDA 134 to access medical devices within a subsequent patient's room. In this way, the caregiver 62 may access and/or control medical devices within a plurality of patient rooms without ever touching the actual medical devices—substantially decreasing the chances of cross-contamination.

As described above, the PDA 134 may supplement or replace the internal screen on the medical device 130. In other words, the information that would otherwise be displayed on the medical device's 130 internal screen would be alternatively displayed on the PDA 134. Although this embodiment has several advantages (as described above) the caregiver 62 would have to periodically hold the PDA 134 in one or both of their hands. As will be appreciated, however, there may be a variety of situations where the caregiver 62 may desire free use of both of their hands while still being able to access and/or control medical devices. Accordingly, FIG. 10 is a diagram of a patient 141, the caregiver 62, and a medical device 140 configured to output to a personal caregiver display 142 in accordance with one embodiment.

Figure 11:
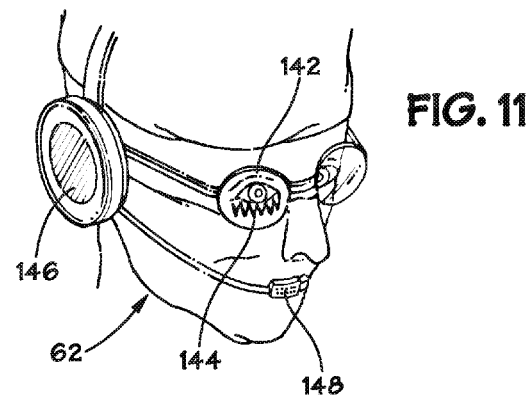
FIG. 11 is an enlarged view of the caregiver of FIG. 10 further including a microphone to interface with the medical device of FIG. 10 in accordance with one embodiment of the present invention.
Figure 10:
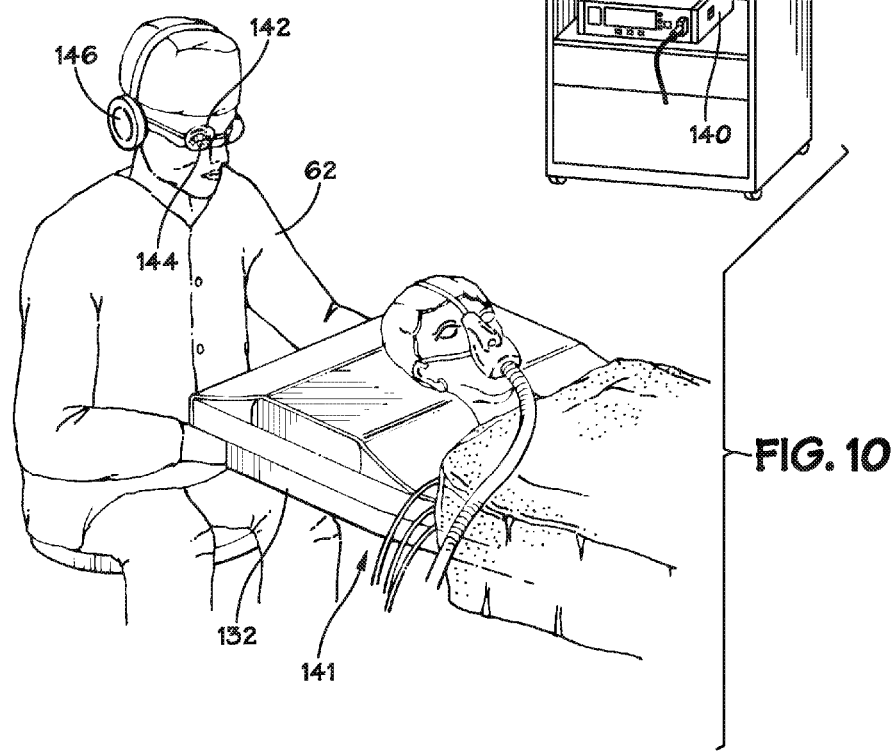
FIG. 10 is a diagram of a patient, a caregiver, and a medical device configured to output to a personal caregiver display in accordance with one embodiment of the present invention.

As illustrated in FIG. 10 and highlighted in an enlarged view in FIG. 11, the caregiver personal display 142 may include a pair of glasses or other suitable wearable optics or eyewear (e.g., a monocular) which may be configured to display outputs from the medical device 140. In one embodiment, the caregiver personal display 142 may be configured to create a transparent or semi-transparent image that the caregiver 62 may be able to view while still being able to see the patient 141. For example, as illustrated in FIGS. 10 and 11, the caregiver personal display may include a pair of glasses with an integral liquid crystal display ("LCD") that may be configured to display a pleth signal 144 while still enabling the caregiver 62 to see the patient 141. In this case, the caregiver personal display 142 effectively creates a "heads-up" display for the caregiver 62, allowing them to see the pleth signal 144 or other suitable medical information as if it were floating in front of them.

It will be appreciated, however, that the illustrated caregiver personal display 142 is merely one potential embodiment of a suitable caregiver personal display. Accordingly, in other embodiments, other types of displays may be employed. For example, in one embodiment, the caregiver personal display may be a video display mounted on a pair of glasses or other mount, which the caregiver 62 may view by shifting his or her focus towards the display. Although medical information in this embodiment may not appear transparent to the caregiver 62, the caregiver 62 may still able to readily access information from the medical device 140 without having the medical device 140 within visual range of the caregiver 62.

As further illustrated in FIGS. 10 and 11, the caregiver personal display may also include a speaker 146 to enable the caregiver 62 to hear alarms or alerts from the medical device 140. Advantageously, the speaker 146 enables the caregiver 62, who is monitoring medical device 140, to hear alerts or alarms without the alarms or alerts bothering other caregiver 62, who may be focused on other activities. In addition, as illustrated in FIG. 11, the caregiver personal display 142 may also include a microphone 148 to enable voice control of the medical device 140, as further described in commonly assigned U.S. patent application Ser. No. 11/540,457 entitled SYSTEM AND METHOD FOR INTEGRATING VOICE WITH A MEDICAL DEVICE and filed on Sep. 29, 2006, which is hereby incorporated by reference.

As described above, secured access and/or patient privacy are both concerns in medical device design. In particular, as medical devices become an increasing vital component of medical treatment, it is important to ensure that only authorized caregivers are able to control these devices. For example, it could be potentially dangerous to a patient if the patient or a patient's guest were able to turn off or adjust a medical device, such as a respirator, a pulse oximeter, a heart/lung machine, and so-forth. Moreover, beyond safety concerns, modern medical devices also typically store a plurality of private personal information regarding the patient, such as social security numbers, addresses, and so-forth. In an age of increasing identity-based crimes, it is advantageous for medical devices to be able to restrict access to this information to approved individuals.

Accordingly, FIG. 12A is a diagram of an exemplary patient room 160 configured to identify caregivers or patients in accordance with one embodiment. As illustrated in FIG. 12A, the hospital room 160 may include a patient bed 162, a medical device 164, and a doorway 166. Moreover, as also illustrated in FIG. 12A, the hospital room 160 may also include the patient 141 and the caregiver 62. As illustrated, the patient 141 may be located in the bed 162 with the caregiver 62 positioned over the patient 141 and in general proximity with the medical device 164.

As illustrated in FIG. 12A, in an embodiment where the medical device 164 is a pulse oximeter, the medical device 164 may include the main unit 12, the display 14, and/or the display 64. Moreover, the medical device 164 may be configured to work in conjunction with an identification ("ID") tag, such as a caregiver ID 168 and/or a patient ID 170 to identify caregivers and/or patients within the hospital room 160. More specifically, in one embodiment, the medical device 164 may be coupled to door sensors 172A and 172B, which are located in close proximity to the door 166 and configured to detect when the caregiver ID 168 and/or the patient ID 170 pass through the doorway 166.

Figure 12B:
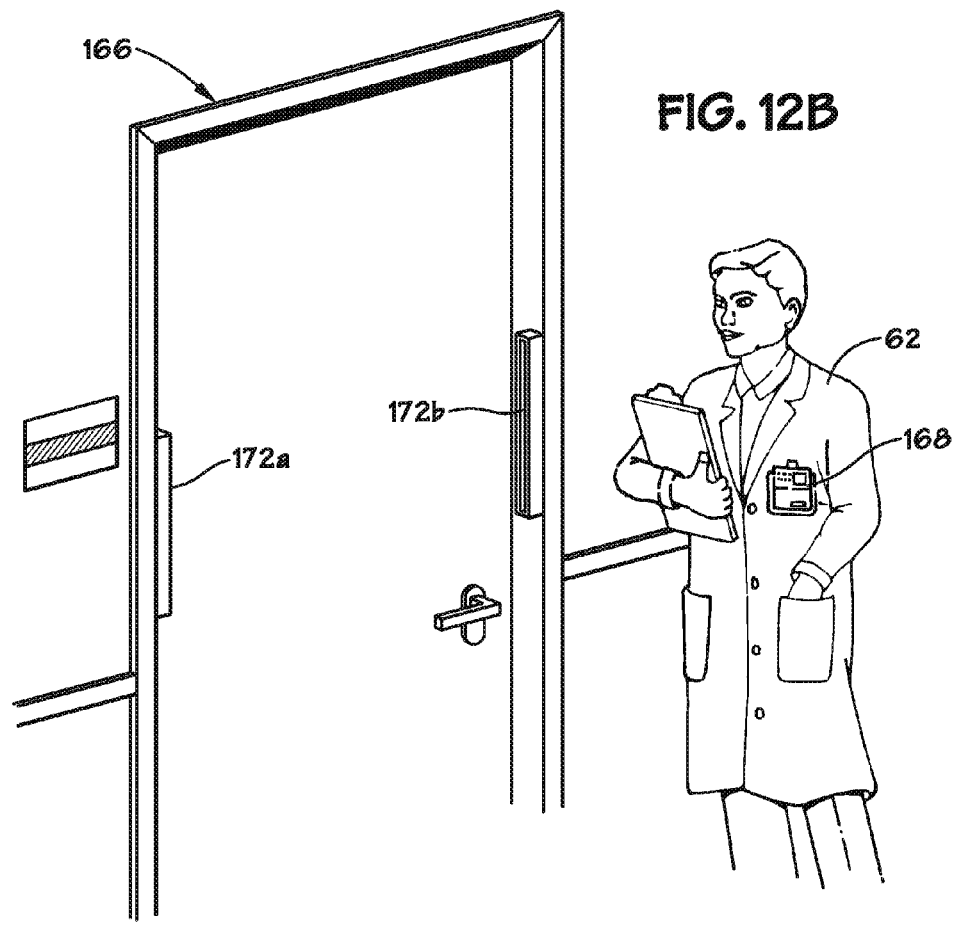
FIG. 12B is an enlarged view of a doorway in a hospital room configured to identify caregivers or patients in accordance with one embodiment of the present invention.
Figure 13:
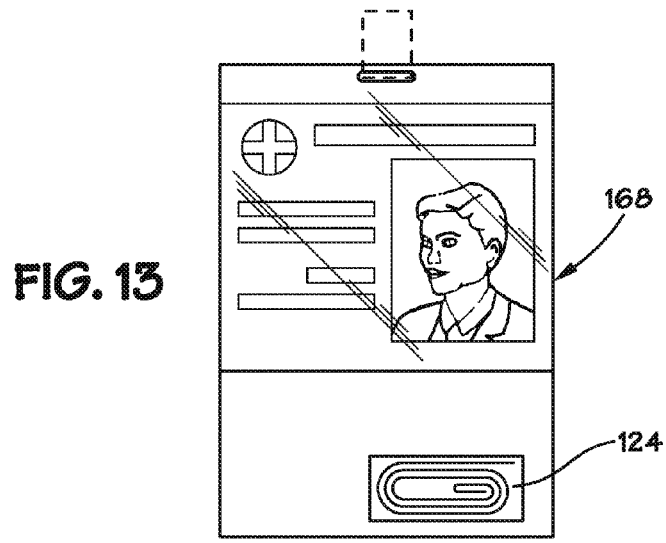
FIG. 13 is a diagram of a caregiver identifier configured to enable caregiver or patient identification in accordance with one embodiment of the present invention.

For example, as illustrated in FIG. 12B, which illustrates an enlarged view of the doorway 166 in accordance with one embodiment, the door sensors 172a and 172b may be configured to detect when the caregiver ID passes through the doorway 166 (e.g., when a caregiver enters or exits the patient room 160). Similarly, the door sensors 172a and 172b may be configured to detect when the patient ID 170 passes through the doorway 166 (e.g., the patient 141 walks or is pushed through the doorway 166). In one embodiment, the door sensors 172a and 172b may include radio frequency ("rf") sensors configured to detect an rf transmitter within the caregiver ID 168 and/or the patient ID 170. For example, FIG. 13 illustrates one embodiment of the caregiver ID 168 including an rf ID tag 174. As will be appreciated the rf ID tag 174 may be a passive rf ID configured to receive transmissions from the door sensors 172a or 172b and to broadcast an identifying signal in response. The door sensors 172a or 172b may detect this identifying signal, and, thus, identify/detect the entry or exit of the caregiver 62 and/or the patient 141.

It will be appreciated, however, that other suitable identification technologies may be employed. For example, in one embodiment, the caregiver ID may be an active ID (e.g., a Bluetooth enabled cell phone). Furthermore, in still other embodiments, the door sensors 172a and 172b may be located elsewhere besides the doors. For example, the sensors 172a and 172b may be located in the ceiling of the patient room 160 and configured to detect when the sensors 168 and/or 170 enter are located in the patient room 160

Figure 14:
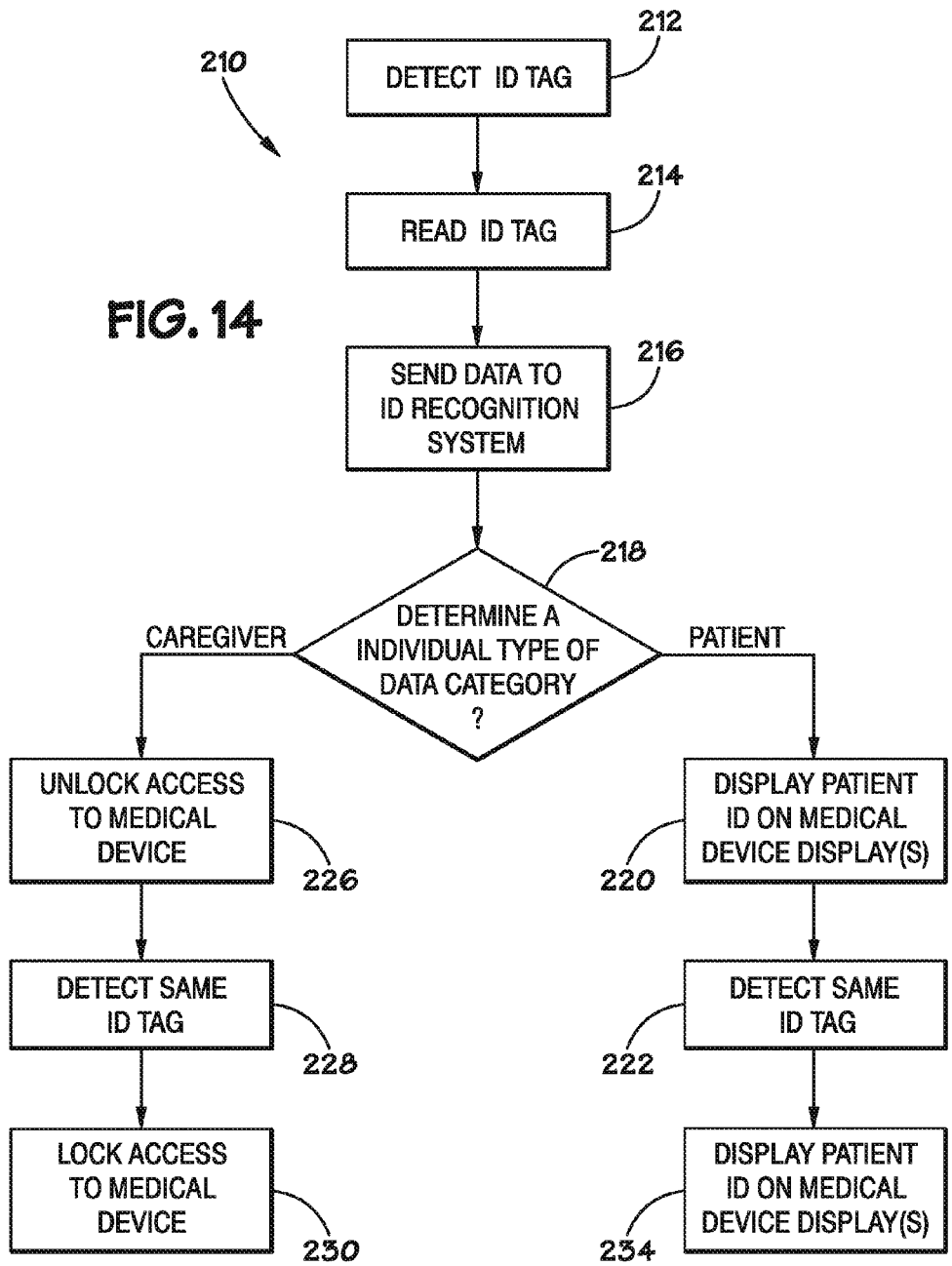
FIG. 14 is a flow chart illustrating an exemplary technique for identifying caregivers or patients in accordance with one embodiment of the present invention.
Figure 15:
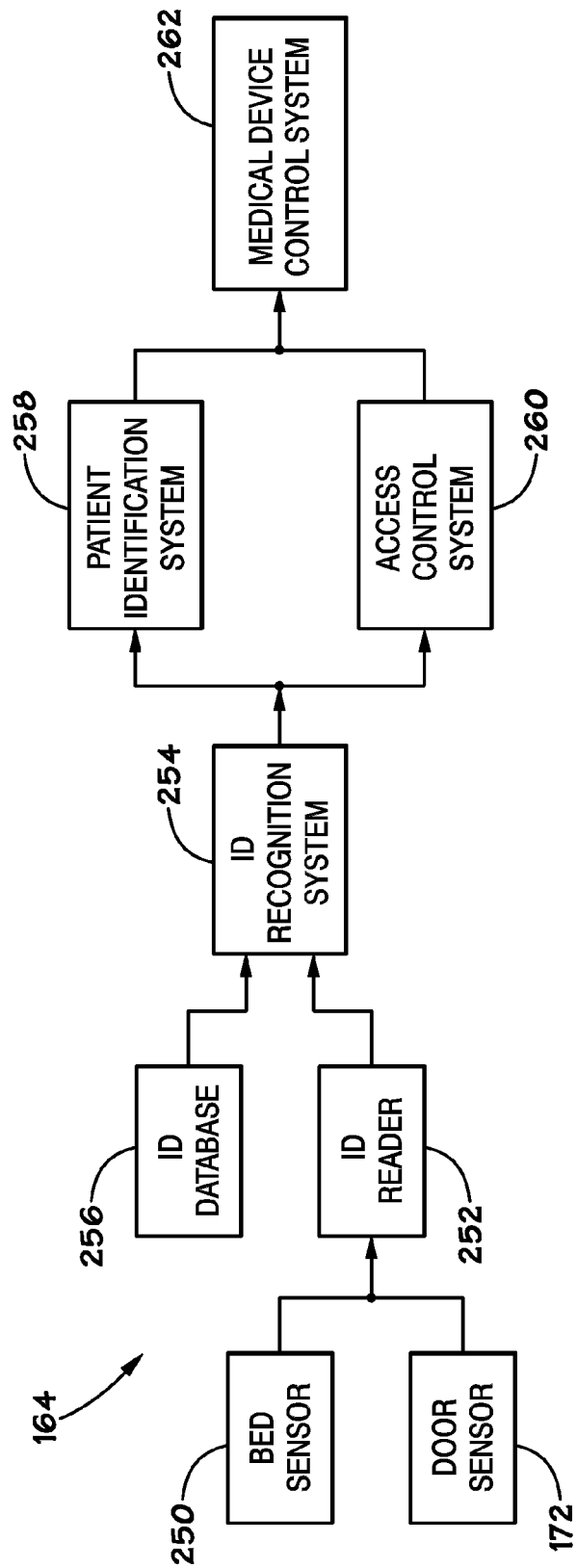
FIG. 15 is a block diagram of an exemplary system for identifying caregivers or patients in accordance with one embodiment of the present invention.

Advantageously, medical device 164 may be configured to utilize this detection information to manage access to its controls and/or to identify the patient 141 for administrative or record keeping purposes. For example, FIG. 14 is a flow chart illustrating an exemplary technique 210 for identifying caregivers or patients in accordance with one embodiment. For ease of description, the technique 210 will be described in conjunction with FIG. 15 which illustrates a block diagram o the medical device 164 in accordance with one embodiment.

As illustrated by block 212 of FIG. 14, the technique 210 may begin by detecting an ID tag. For example, in one embodiment, the door sensors 172 may detect the caregiver ID 168 or the patient ID 170. In another embodiment, the medical device 164 may alternatively or additionally include a bed sensor 250 to detect the ID tag. More specifically, the bed sensor 250 may be mounted on the patient bed 162 and configured to detect the patient ID 170. The bed sensor 250 may be particularly advantageous in hospital rooms including multiple patient beds 162, as the door sensors 172 may not be able to determine which of the plurality of patient beds 162 a particular patient is occupying. Moreover, the bed sensor 250 may also be configured to detect the patient ID 170 and to communicate patient identification information to the medical device 164, as set forth in further detail below.

Next, the technique 210 may include reading the detected ID tag, as indicated in block 214. For example, in one embodiment, an ID reader 252 may be configured to read the identity information from the caregiver ID 168 and/or the patient ID 170. Next, the technique 210 may include sending the identity information from the ID tag to an ID recognition system, as indicated in block 216. For example, in one embodiment, the ID reader 252 may transmit the identity information to an ID recognition system 254.

Next, the technique 210 may include determining an individual type of the detected ID tag, as indicated by block 218. For example, in the illustrated embodiment of the technique 210, the technique may include determining whether the detected ID tag corresponds to the caregiver 62 or the patient 141. In one embodiment, the ID recognition system 254 may make this determination based on an ID database 256, which includes information regarding a plurality of ID tags and the individual type corresponding to each of the plurality of ID tags. Alternatively, the individual type may be encoded on the caregiver ID 168 or the patient ID 170 and communicated to the ID recognition system 254 via the door sensor 172 and/or the bed sensor 250. Although the technique 210 is illustrated in FIG. 14 as including two branches, one for caregivers and one for patients, it will be appreciated that this is merely exemplary. As such, in alternate embodiments, the technique 210 may include multiple branches for various suitable individual types. For example, the technique 210 may respond differently to different types of caregivers, such as doctors, nurses, orderlies, and so-forth.

Returning now to FIG. 14, if the ID tag corresponds to a caregiver, the technique 210 may next include unlocking access to the medical device at an appropriate permissions level. For example, in one embodiment, an access control system in the medical device 164 may be configured to unlock the medical device 164 and allow the medical device control system 262 to execute instructions and/or commands commensurate with the permission level of the caregiver 62.

The technique 210 may then continue to allow the caregiver 62 to execute commands until the same ID tag is again detected by the door sensor 172 or the bed sensor 250, as indicated by block 228 (i.e., the caregiver leaves the patient room 160). Alternatively, the door sensors 172a and 172b may be configured to detect when the caregiver ID 168 leaves the proximity of the sensor. In this embodiment, rather than detecting when the caregiver ID 168 crosses their threshold, the door sensors 172a and 172b may be configured to detect when the caregiver ID 168 is located within a certain distance of the door sensors 172a and 172b (i.e., the caregiver is located in the patient room 160).

Upon detecting the exit of the caregiver 62, the technique 210 may include locking further access to the medical device 164 to prevent the patient 141 or other unauthorized individuals from adjusting the medical device 164 in the absence of the caregiver 162 (block 230). In this way, the technique 210 enables the medical device 164 or other suitable medical device automatically unlock when the caregiver 62 enters the patient room 160, to accept commands freely from the caregiver 62 while they are in the room, and then to relock automatically when the caregiver 62 leaves the patient room. Moreover, in one embodiment, the medical device 164 may be configured to record which caregiver 62 gave which commands to the medical device 164, because each caregiver in a hospital may be assigned a unique caregiver ID 168. In this way, it may be possible for a hospital to reconstruct patient treatment history, if desired.

Returning again to block 218 of FIG. 14, if the individual type is determined to be a patient, the technique 210 may include displaying a patient ID on a display of the medical device 164, as indicated by block 220. In one embodiment, a patient identification system 258 within the medical device 164 may be configured to display the patient ID on the display 14. Furthermore, the medical device 164 may also be configured to annotate any patient medical data subsequently stored by the medical device 164 with the patient information.

Next, if the same ID tag is detected again (or contact with the ID tag is lost, as described above), the technique 210 may include clearing the patient information from the medical device 164, as indicated by blocks 222 and 224. Accordingly, the medical device 164 may be able to automatically identify the identity of patients being monitored or treated without the need for caregivers to manually enter this information into the medical device 164. Advantageously, this reduces the chances of cross-contamination and automates one additional caregiver function.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to pulse oximeters, but also to other suitable medical devices, such as respirators, ventilators, EEGs, EKGs, and so-forth.

What is claimed is:

1. A medical device comprising:
   a reader configured to read identification information from an identification tag; and
   a patient identification system configured to store the identification information in the medical device as patient information; wherein the patient identification system is configured to associate the patient information with medical data produced by the medical device, wherein the patient identification system is configured to clear the patient information from the medical device if contact with the identification tag is lost.

2. The medical device of claim 1, comprising a sensor configured to detect an identification tag.

3. The medical device of claim 2, wherein the sensor comprises a bed sensor configured to be mounted in proximity to a patient bed.

4. The medical device of claim 2, wherein the sensor comprises a door sensor configured to be mounted in proximity to a doorway.

5. The medical device of claim 2, wherein the sensor comprises an rf ID tag.

6. The medical device of claim 1, comprising a display, wherein the medical device is configured to display the patient information on the display.

7. A method for accessing a medical device, comprising:
   reading identification information from an identification tag; and
   storing identification information in the medical device as patient information of a patient identification system; and
   clearing the patient information from the medical device if contact with the identification tag is lost.

8. The method of claim 7, comprising associating the patient information with patient medical data produced by the medical device.

9. The method of claim 7, comprising displaying the patient information on a display of the medical device.

10. The method of claim 7, wherein the identification rag comprises an rf ID tag and reading identification information comprises detecting the rf ID tag.

11. The method of claim 7, comprising determining if the identification tag corresponds to a patient or a caregiver.

12. The method of claim of claim 7, comprising sending the identification information to an identification recognition system.

13. A medical device, comprising:
    a reader configured to read identification information from an identification tag; and
    a patient identification system configured to annotate patient medical data produced by the medical device with patient information stored from the identification information, wherein the patient identification system is configured to clear the patient information from the medical device if contact with the identification tag is lost.

14. The medical device of claim 13, wherein the patient identification system is configured to send the identification information to an identification recognition system.

15. The medical device of claim 14, wherein the identification recognition system is configured to determine a type of the identification tag based on an identification database.

16. The medical device of claim 13, comprising a display, wherein the patient identification system is configured to display the patient information on the display.

17. The medical device of claim 13, comprising a sensor configured to detect an identification tag.

18. The medical device of claim 17, wherein the identification tag comprises an rf ID sensor configured to receive a transmission from the sensor and broadcast an identifying signal in response.

* * * * *